United States Patent
Zickmann et al.

(10) Patent No.: US 6,726,481 B1
(45) Date of Patent: Apr. 27, 2004

(54) DENTAL IMPLANT

(76) Inventors: Albert Zickmann, 5455 N. Sheridan Rd. #3608, Chicago, IL (US) 60640; Sheldon Leonard, 6 Cedar La., Cedarhurst, NY (US) 11516

( * ) Notice: Subject to any disclaimer, the term of this patent is extended or adjusted under 35 U.S.C. 154(b) by 104 days.

(21) Appl. No.: 10/084,441

(22) Filed: Feb. 28, 2002

Related U.S. Application Data

(63) Continuation of application No. 09/606,826, filed on Jun. 28, 2000, now abandoned.

(51) Int. Cl.⁷ .................................................. A61C 8/00
(52) U.S. Cl. ....................................................... 433/173
(58) Field of Search ................................ 433/172, 173, 433/174, 175, 176

(56) References Cited

U.S. PATENT DOCUMENTS

| | | | |
|---|---|---|---|
| 4,856,994 A | 8/1989 | Lazzara et al. | 433/173 |
| 5,152,687 A | 10/1992 | Amino | 433/173 |
| 5,458,488 A | 10/1995 | Chalifoux | 433/173 |
| 5,533,898 A | 7/1996 | Mena | 433/173 |
| 5,873,722 A | 2/1999 | Lazzara et al. | 433/173 |

FOREIGN PATENT DOCUMENTS

| | | |
|---|---|---|
| FR | 2 743 291 | 11/1997 |
| GB | 2 193 640 | 2/1988 |
| WO | WO 98/31296 | 7/1998 |

Primary Examiner—John J. Wilson
(74) Attorney, Agent, or Firm—Raymond Van Dyke; Nixon Peabody LLP

(57) ABSTRACT

An endosseous dental implant system having an implant body and an abutment. The implant body has a tapered cylindrical surface near its top end and an internally threaded or unthreaded passage extending into the implant body through an opening at the top of the implant. The abutment has an internal passage for receiving a fastener or, alternatively has a fastener as part of the abutment. The fastener threads into the implant body so that a tapered cylindrical cavity in the abutment mates with a matching tapered cylindrical surface of the implant to form an anti-rotational and locking junction with the implant when fastened by a screw or fastener. In addition to the anti-rotational and locking junction formed by the mating of external tapered cylindrical surface and internal tapered cylindrical surface, the dental implant system may also include an implant body having a multi-sided projection. In this embodiment, the abutment has a cavity for receiving the projection. The cavity and projection forms an additional anti-rotational junction between the implant body and the abutment.

12 Claims, 11 Drawing Sheets

DENTAL IMPLANT

RELATED APPLICATIONS

This application is a continuation application of U.S. patent application Ser. No. 09/606,826, filed on Jun. 28, 2000, now abandoned incorporated herein by reference.

BACKGROUND OF THE PRESENT INVENTION

1. Field of the Invention

This invention relates to a dental implant system. More particularly, this invention relates to a dental implant system having an implant body and an abutment, wherein the implant body and abutment format least a first anti-rotational connection by frictional engagement of mating tapered surfaces.

2. Background of the Invention

Two-part endosseous dental implant systems for insertion in a wholly or partially edentulous region of the jawbone of a patient are known in the art. The implant systems may be completely embedded in a jawbone of a patient. Typically, a protective cover screw is attached to the top of the implant. The implant is then covered with mucosal tissue. Alternatively, the implants or a protective component affixed to the implant may protrude through the oral mucosa at the time of placement of the implant into the jawbone. Typically, the implants are permitted to remain in place while new bone grows around the implant. Once the implant has become firmly anchored in bone, the mucosal tissue must be reopened if the implant is covered. The protective component is then removed and an abutment or post is connected to the implant using a screw. A prosthesis can then be connected to the abutment or post.

Many two-part implant systems have an external, hexagonal projection, sometimes called a male hex, which projects upwardly from the top end of the implant. A shoulder surrounds the base of the male hex. An abutment or post having an outer diameter that substantially matches the outer diameter of the implant is seated on the male hex to form a substantially sealed connection. Some implants have an externally-threaded sidewall portion that can be screwed into an opening formed in the bone after bone tissue has been removed from the jawbone. Examples of such an implant may be found in U.K. Patent No. 1,291,470 or in U.S. Pat. No. 4,713,004. With implant systems of this kind, the male hex projection at the top of the implant is designed to engage an inserting device, e.g. a wrench, that is used to insert the implant in the jawbone.

Another kind of two-part, endosseous dental implant system with an external male hex is a cylindrical implant having a non-threaded, external body portion. These implants are pushed into an opening formed in bone tissue. An example of this type of implant is a BIO-VENT® implant available from Core-Vent Corporation, 15821 Ventura Boulevard, Suite 420 Encino, Calif. 91436.

In implants having external male heads, the male head is used to attach the implant to an abutment or post having a matching female hex-shaped cavity that receives and engages the male hex projection. Such male hex heads and female hex cavities are sometimes referred to as coupling surfaces. Typical implant systems have external male hexes and mating internal female hex cavities with walls of the hexagonal head and the hex-shaped cavity of the abutment being perpendicular to a longitudinal axis of the abutment and parallel to one another.

With such implant systems, the male hex of the implant is smaller in diameter than the diameter of the hex-shaped cavity of the abutment to permit the male hex to fit inside the female cavity. The difference in diameter is sufficiently large to allow for manufacturing variations while still allowing the coupling surfaces of the abutment to seat fully on the shoulder of the implant. Seating the coupling surfaces on the shoulder of the implant creates a sealed outer margin between abutment and implant. However, this leaves space between the coupling surfaces of the male and female hexes.

Within the hex head region, and extending into the implant itself, there is in such implants a threaded hole for receiving an attachment screw of a mating abutment. The abutment typically has an interior abutment passage centered on its hex cavity. When attaching the abutment to the implant, the screw is inserted through the abutment passage and is screwed into the threaded implant hole. Tightening the screw tightens the abutment against the implant. When the screw is tightened until the external hex of the implant mates with the matching female hex cavity in the abutment, the system is secured against axial displacement of the abutment from the implant.

The seating of the external hex of the implant within the female hex cavity of the abutment, where both the external hex and the internal hex cavity have parallel walls, results in the full seating of the abutment onto the shoulder surrounding the external male hex of the implant. However, according to reported studies, the seating of the external hex of the implant within the female hex cavity of the abutment of existing implant systems fails to completely prevent rotational displacement of the implant with respect to the abutment.

For example, a scientific study presented by Dr. Paul Binion at the Academy of Osseointegration meeting in San Diego, Calif. in Mar. 1993, documented that the coupling surfaces of commercially-available implants allow four to five degrees of rotation between the abutment and the implant. Dr. Binion later reported that certain implant/abutment assemblies exhibit up to nine degrees of rotation between the implant and the abutment. The relative rotation of the abutment and implant result in an attachment that is unstable. Lateral forces from biting are transmitted to the screw joining the abutment to the implant rather than the coupling surfaces of the external hex projection on the implant and the internal hex cavity in the abutment. As a result, the screw that joins the implant to the abutment may break or loosen. Rotational instability may also adversely affect the accuracy of transfer procedures needed for the indirect fabrication of a final prosthetic restoration on such implant/abutment assemblies.

Attempts have been made to remedy the problem of rotational instability in implant/abutment assemblies. For example, U.S. Pat. No. 4,547,157 discloses an implant having a conical projection for mating with an abutment having a matching cavity. A small degree of taper of the two surfaces results in a friction fit between the parts that tends to maintain the connection. These systems do not use a screw that passes through the abutment to lock the abutment to the implant. The tapered, cylindrical coupling surface makes direct contact and fully seats on the mating cavity in the implant, which results in a good connection. However, a drawback with this type of connection is that a ledge is formed as the outer walls of the internal cavity fit over the conical projection of the implant. This ledge can trap food particles and irritate gum tissues. Moreover, it is necessary to use a hammering action to seat the abutment onto the implant, which is uncomfortable for a patient. Further, it is not possible to quantify the force of hammering, which varies greatly from one practitioner to the other.

Other implants exist that have an internal taper connection. One example is the ITI® Dental Implant System available from Straumann Holding AG, CH-4437 Waldenburg, which has a very wide implant head to accommodate the abutment. Therefore, the ITI® dental implant is not suitable for narrow spaces. In addition, the marginal area of the restoration is cemented directly onto the implant. As a result, the top of the implant must remain exposed after healing of the soft tissues. A disadvantage of this arrangement is that it is not possible to modify the marginal area, which leaves a visible unaesthetic silver margin around the restoration.

There is, therefore, a need for improvements in dental implant systems, particularly, endosseous dental implant systems which overcome the above and other disadvantages.

SUMMARY OF THE INVENTION

The present invention is directed to an endosseous dental implant system that includes at least two parts: a first part called a implant body, and a second part called an abutment, post or insert. The implant body may have a threaded external sidewall surface or a non-threaded external sidewall surface, and the implants themselves may be generally cylindrical or tapered in shape. The external sidewall surface may also have one or more longitudinally extending grooves.

A part or all of the external surfaces of the implant system may be treated by applying a coating consisting of hydroxyl apatite or titanium plasma spray. Alternatively, part or all of the external surfaces may be roughened by blasting or acid etching or a combination of the above-mentioned methods.

A tapered cylindrical surface is provided at the top end of the implant body for engaging and interlocking anti-rotationally with a matching tapered cavity inside the abutment. The anti-rotational connection is formed when the abutment is fully seated and fastened to the implant body by means of screw or fastener. On top of the implant, there may be an additional projection, preferably a multi-sided projection. In the preferred embodiment, the projection consists of multiple sides that are parallel to the longitudinal axis of the implant body. The optional projection forms a second anti-rotational connection with a corresponding internal cavity in the abutment.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
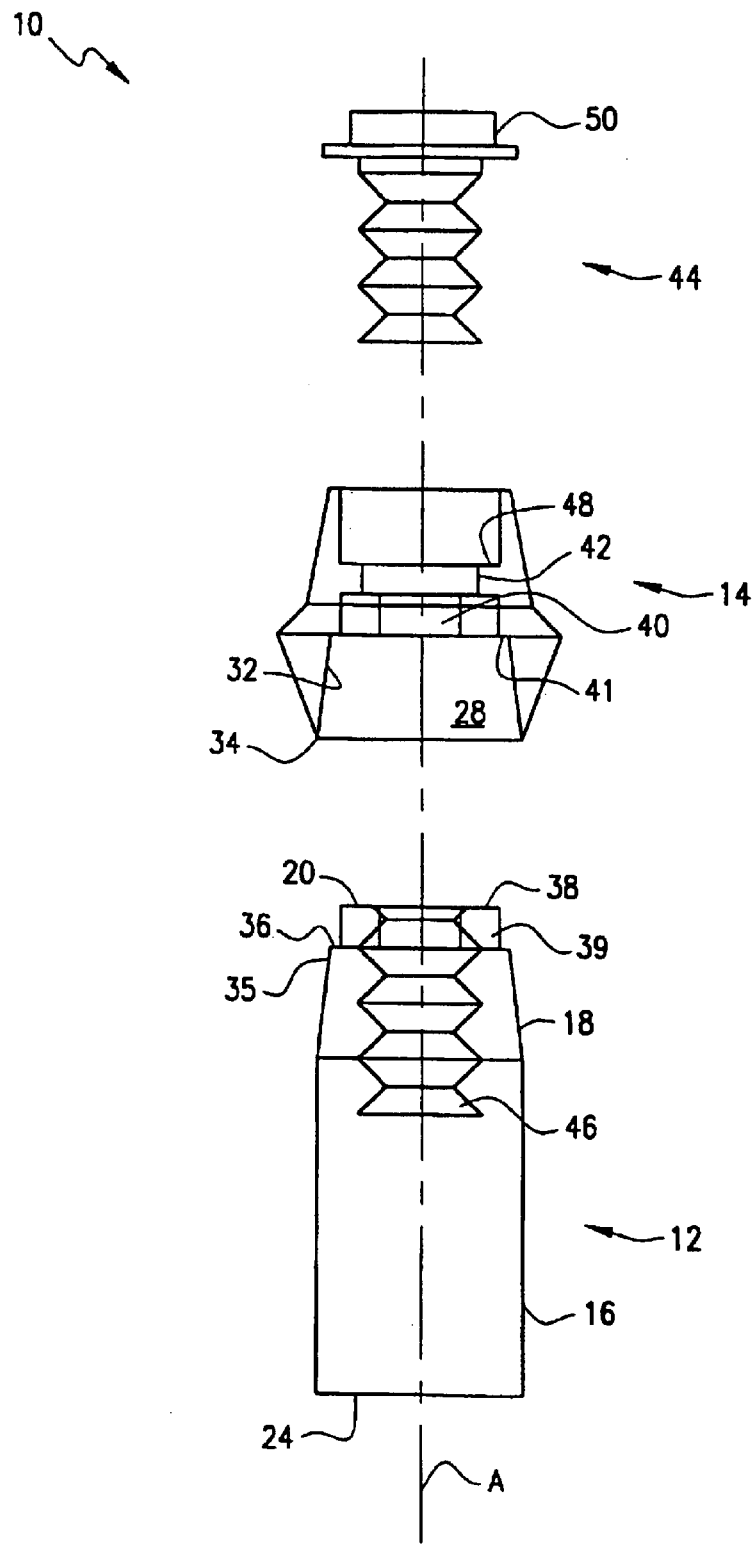
FIG. 1 is an exploded cross-sectional side view of a first embodiment of the dental implant system of the invention.
Figure 2:
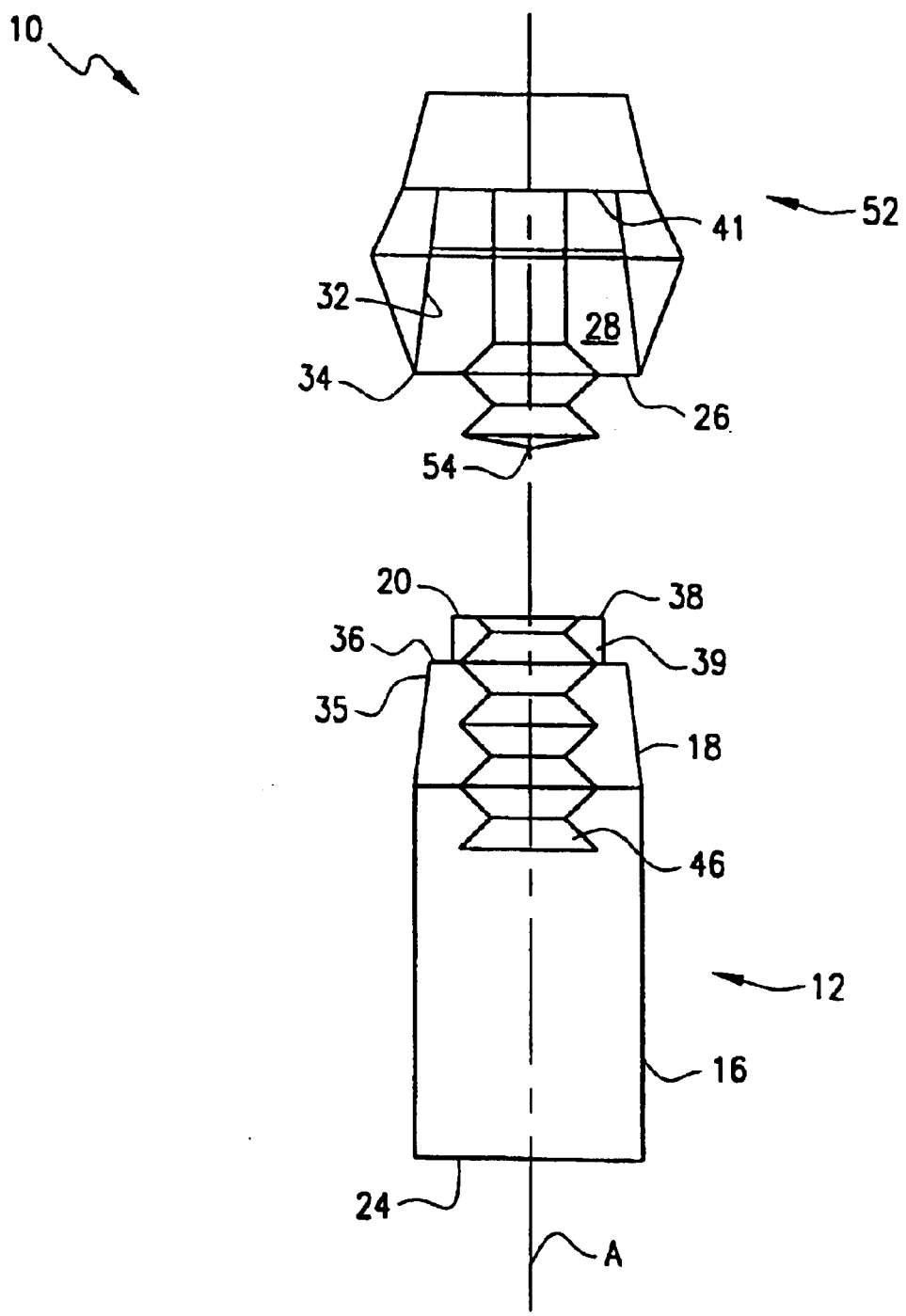
FIG. 2 is an exploded cross-sectional side view of a second embodiment of the dental implant system of the invention.
Figure 3:
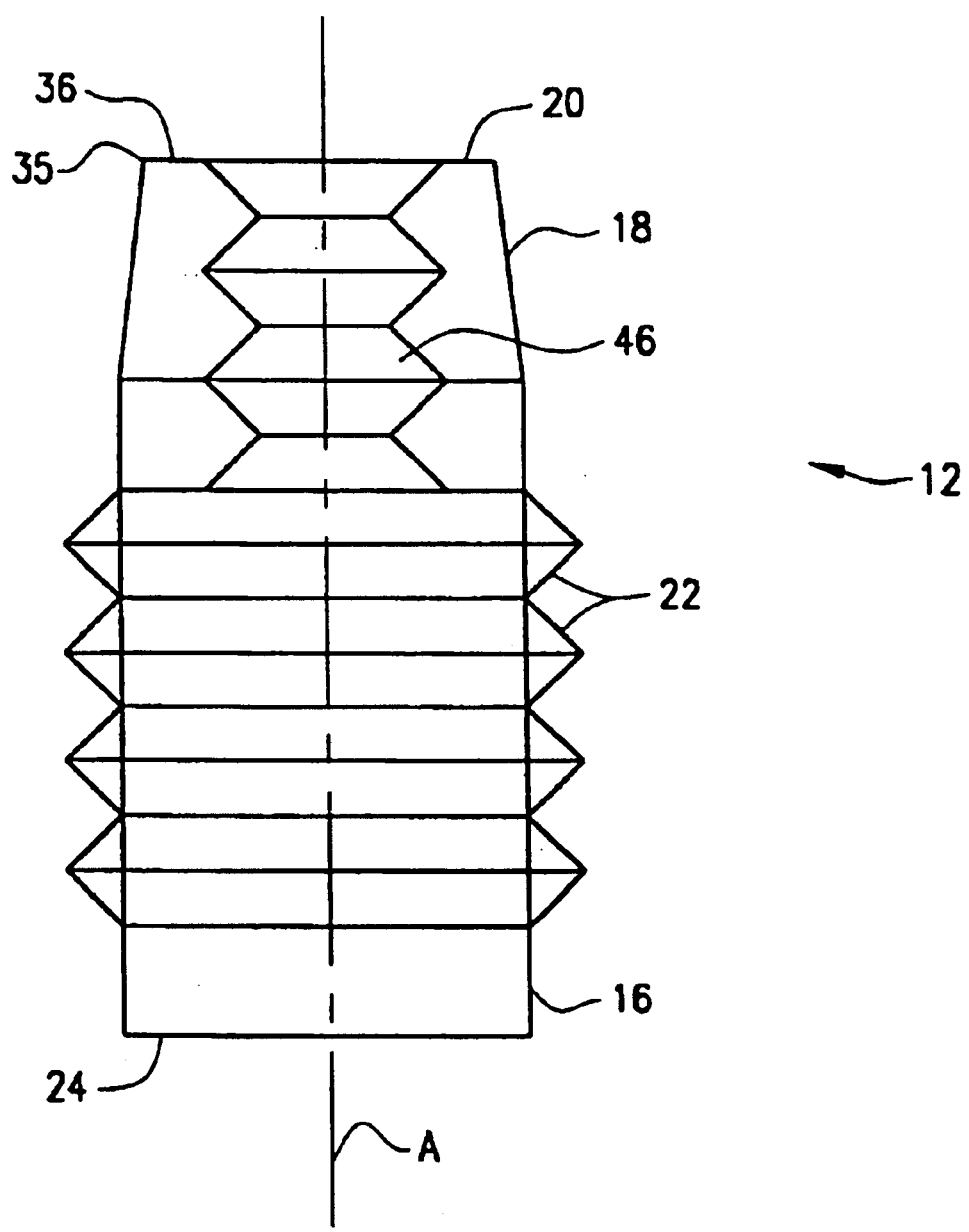
FIG. 3 is a cross-sectional side view of an embodiment of a threaded implant body that may be used with the dental implant system of FIGS. 1 and 2.
Figure 4:
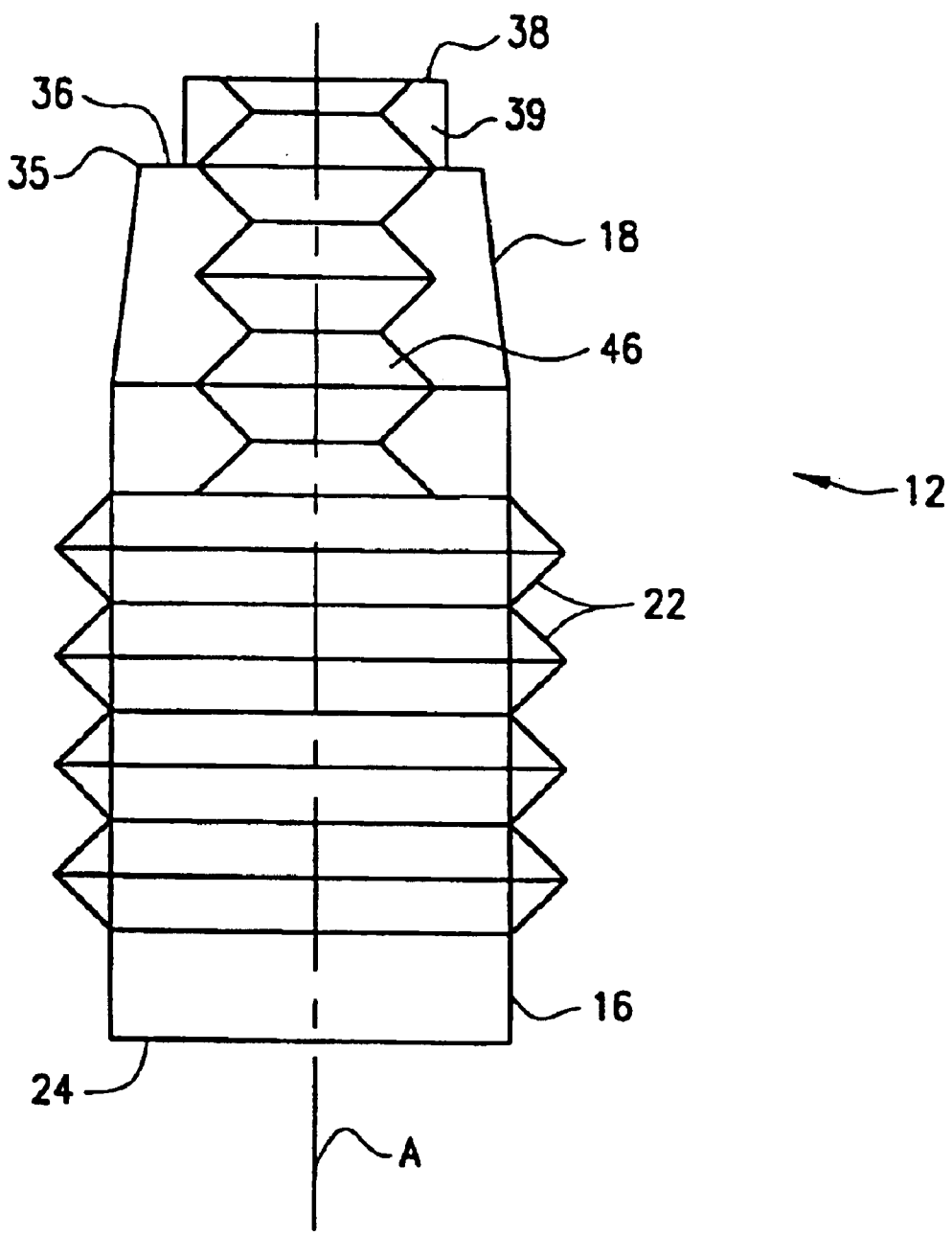
FIG. 4 is a cross-sectional side view of another embodiment of a threaded implant body that may be used with the dental implant system of FIGS. 1 and 2.

Referring now to FIGS. 1–4, shown is a multi-part, endosseous dental implant system, generally designated by the reference numeral 10. It should be understood that common components of the various embodiments for practicing the instant invention retain the same numerical designation in each of the Figures. The dental implant system 10 has an implant body, generally designated by the reference numeral 12 (FIGS. 1–4), and an abutment, generally designated by the reference numeral 14 (FIGS. 1 and 2).

With reference now to FIG. 1, the implant body 12 has an external sidewall 16 having a generally-cylindrical shape, and an external tapered cylindrical surface 18 that tapers towards top end 20 of implant body 12. In one embodiment, the external sidewall 16 of the implant body 12 may include a plurality of external screw threads 22, as illustrated and described in more detail in connection with FIGS. 3 and 4, having a substantially constant pitch. The external screw threads 22 may be either self-tapping or non-self-tapping, as is understood in the art. The external screw threads 22 may extend along the entire length of external sidewall 16 or only partly along the length of the external sidewall 16. The external sidewall 16 of the implant body 12 above the external screw threads 22 may either be substantially cylindrical, may taper upwardly and outwardly or may taper upwardly and inwardly toward the top end. Additionally, at the bottom end 24 of the implant body 12, the external sidewall 16 of the implant body 12 may be substantially cylindrical, or may taper toward the bottom end 24 of the implant body 12.

With reference now to FIG. 1, abutment 14 preferably has a generally tapered shape also. The bottom end 26 of the abutment 14 has a primary cavity 28 therein to receive the aforedescribed top end 20 of the implant body 12 when the abutment 14 is seated on implant body 12.

Figure 5:
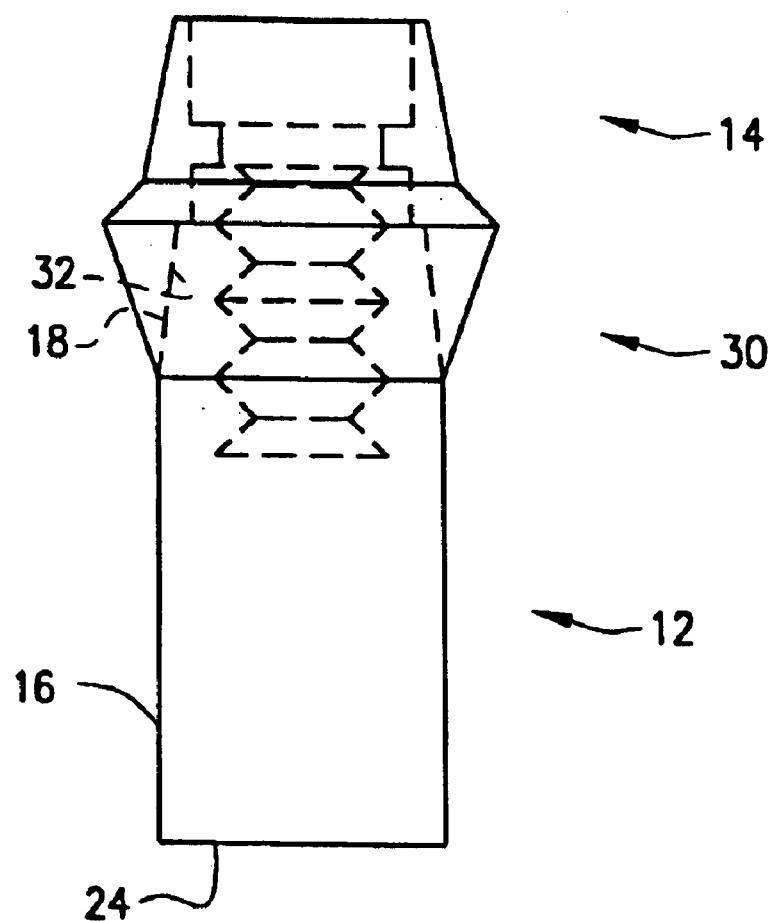
FIG. 5 is a cross-sectional side view of the components of the dental implant system of FIG. 1 assembled.

When implant body 12 and abutment 14 of the instant invention are secured together, at least one anti-rotational component 30 or connection is formed, as illustrated in FIG. 5. The first anti-rotational connection 30 is formed in part by the aforedescribed external tapered cylindrical surface 18 of the implant body 12. As illustrated in FIG. 1, the external tapered cylindrical surface 18 tapers upwardly and inwardly near the top end 20 of the implant body 12. The external tapered cylindrical surface 18 frictionally engages a mating internal tapered cylindrical surface 32 within the primary cavity 28 of the abutment 14 when components 12 and 14 are fully seated and form the first anti-rotational connection 30. As is well understood to those skilled in the art, friction between the external tapered cylindrical surface 18 and the internal tapered cylindrical surface 32 increases as the abutment 14 is fastened to the implant body 12. As shown in FIG. 1, the abutment 14 has an outer diameter 34 at the bottom end 26 of the abutment 14 that is substantially the same as the outer diameter 35 of the top end 20 of the implant body 12 before installation of the abutment 14 on the implant body 12.

Preferably, the degree of taper of the external tapered cylindrical surface 18 of the implant body 12 and the corresponding internal tapered cylindrical surface 32 on the inside of the abutment 14 is in the range of about one to about eight degrees.

Implant body 12 preferably has a flat surface 36 on top end 20, as shown in FIG. 1. The flat surface 36 of the implant body 12 is perpendicular to a longitudinal axis A of the implant body 12. Preferably, the flat surface 36 should not make contact with the abutment 14 when the implant body 12 is secured to the abutment 14. Instead, the external tapered cylindrical surface 18 and the internal tapered cylindrical surface 32 should mate to create the aforementioned first anti-rotational connection 30. When the abutment 14 is fully seated, space between the bottom end 26 of the abutment 14 and the top end 20 of the implant body 12 is completely sealed off from the environment.

In one embodiment, as illustrated in FIGS. 1, 2 and 4, 5, 7, and 11 a second anti-rotational connection is formed by a projection 38 from the top end 20 of implant body 12 that preferably has a substantially flat upper surface thereof. The projection 38 has a plurality of sidewall surfaces, generally designated by the reference numeral 39, and numbering four (square) to eight (octagon) most preferably six (hexagon).

In preferred embodiments, the projection 38 is sized to fit inside a secondary cavity 40, as illustrated in FIG. 1, located on an upper internal surface 41 of the primary cavity 28 inside of abutment 14, thereby creating a second anti-rotational connection by the frictional interface of the projection 38 into the secondary cavity 40. The anti-rotational property of the second anti-rotational connection is, however, not typically adequate to prevent all rotational movement of abutment 14, although enough to locate the position of the abutment 14 with sufficient accuracy for further restoration with a prosthetic component.

With reference again to FIG. 1, the abutment 14 may include an abutment passage 42 therein. Abutment passage 42 is preferably cylindrically-shaped for receiving a fastener, generally designated by the reference numeral 44, therein which passes through the abutment 14. The fastener 44 may be a screw, bolt, or other suitable device for securing abutment 14 to implant body 12. The fastener 44 preferably passes through the aforementioned abutment passage 42 and preferably screws into a threaded implant passage 46 in the implant body 12. The threaded implant passage 46 in the implant body 12 extends downwardly into the implant body 12 from the top end 20, and is preferably substantially centered through the aforedescribed projection 38 at the top end 20 of the implant body 12. A flange surface 48, as shown in FIG. 1, is preferably provided in the abutment 14 for engaging a head portion 50 of the fastener 44. Tightening of the fastener 44 seats the abutment 14 substantially fully upon the implant body 12, thereby creating the aforementioned first anti-rotational connection, as illustrated by the conjoined component 30 in FIG. 5. Additionally, in certain embodiments of the invention, tightening of the fastener 44 additionally creates the second anti-rotational connection.

In a further alternate embodiment, illustrated in FIG. 2, a modified abutment, generally designated by the reference numeral 52, may have an attached fastener portion 54 that extends from the aforementioned upper internal surface 41 of the primary cavity 28. The attached fastener 54 screws into the aforedescribed threaded implant passage 46 in the implant body 12. Tightly securing the modified abutment 52 to implant body 12 with the attached fastener 54 seats the modified abutment 54 upon the implant body 12 and frictionally engages the internal and external tapered cylindrical surfaces 18, 32 of the modified abutment 52 and implant body 12, respectively, thereby creating the aforementioned first anti-rotational connection.

Figure 6:
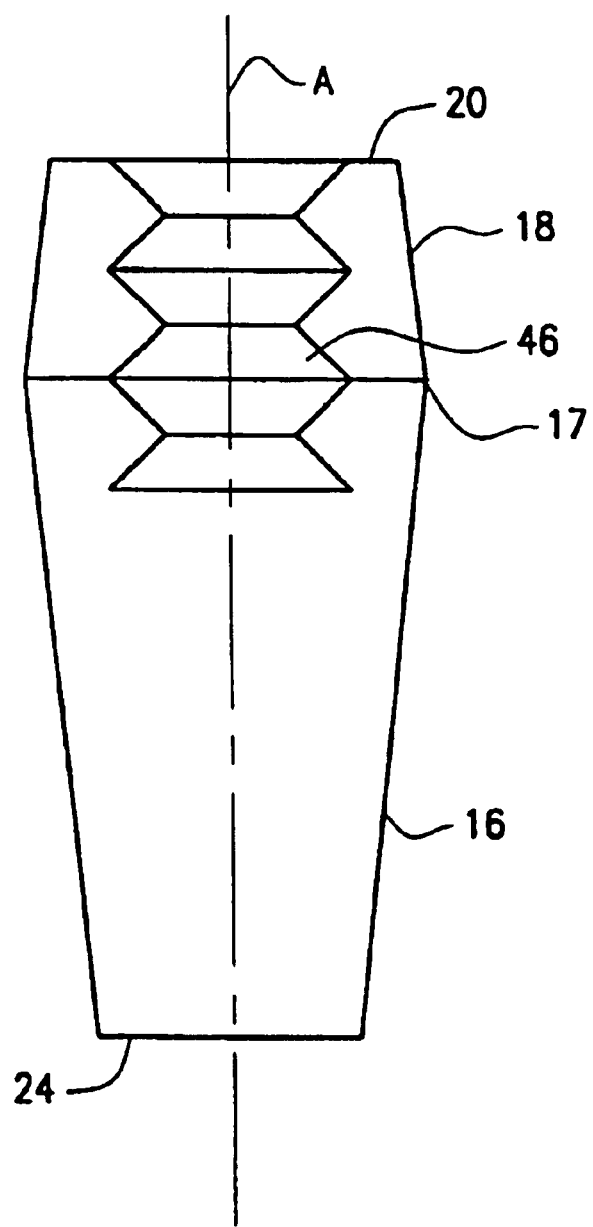
FIG. 6 is a cross-sectional side view of an alternate embodiment of a tapered implant body pursuant to the teachings of the present invention.

With reference now to FIG. 6, there is illustrated an alternate embodiment of the present invention in which the external sidewall 16 of the implant body 12 is tapered inward toward axis A, as opposed to the substantially cylindrically-shaped configuration of the external sidewall 16 illustrated in FIGS. 1–5. As shown in FIG. 6, external sidewall 16 and the external tapered cylindrical surface 18 meet at a juncture 17. In one embodiment, the radial diameter of the external sidewall 16 at the bottom end 24 of the implant body 12 is less than the radial diameter of the external tapered cylindrical surface 18 at the top end 20 of the implant body 12.

Figure 7:
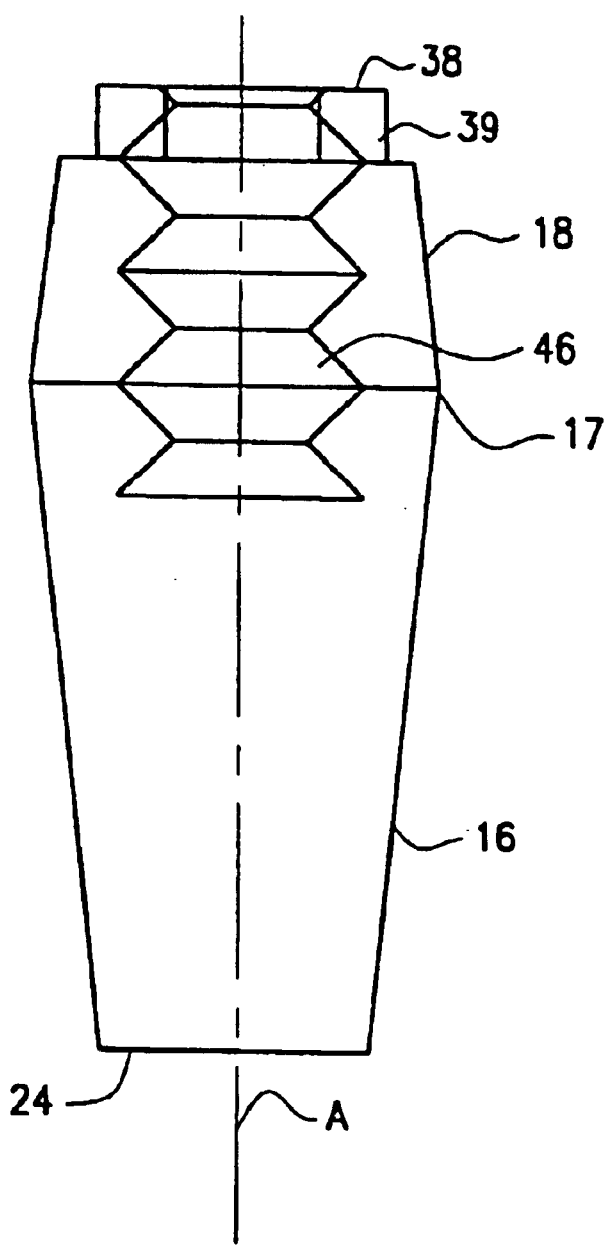
FIG. 7 is a cross-sectional side view of the tapered implant body of FIG. 6 with a projection affixed thereto.

With reference now to FIG. 7, there is illustrated a modified version of the embodiment shown in FIG. 6 having a projection 38 affixed at said top end 20 of implant body 12 and having hexagonal walls 39.

Figure 8:
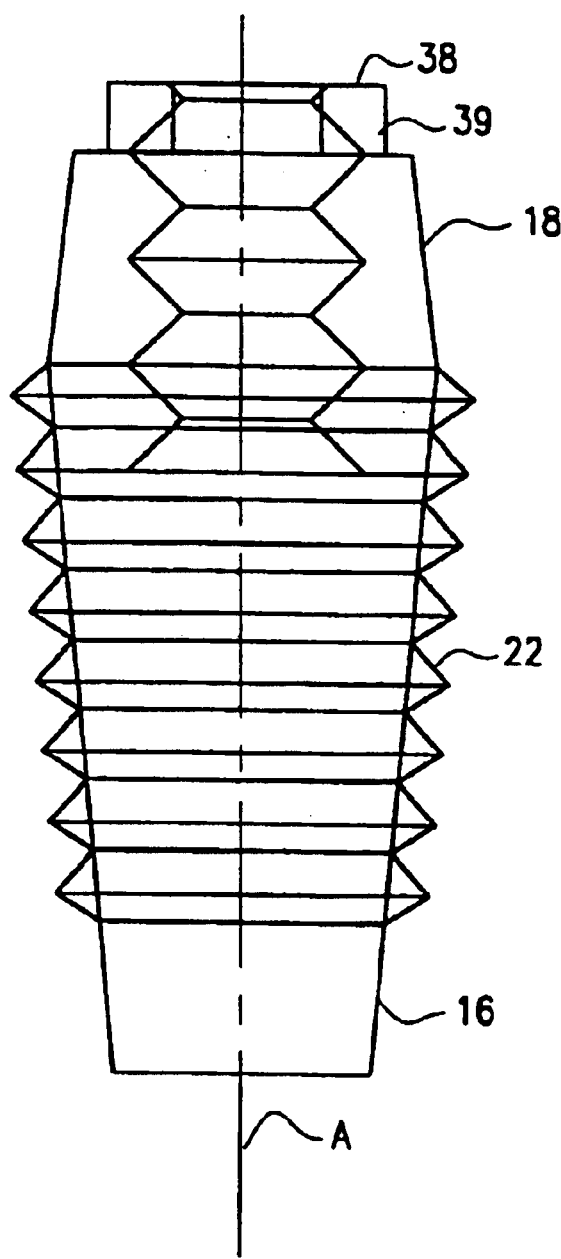
FIG. 8 is a cross-sectional side view of the tapered implant body of FIG. 7 with threads.

With reference now to FIG. 8, there is shown a still further modified version of the embodiment shown in FIG. 7 having external screw threads 22 along said external sidewall 16 of the implant body 12 for engaging bone.

Figure 9:
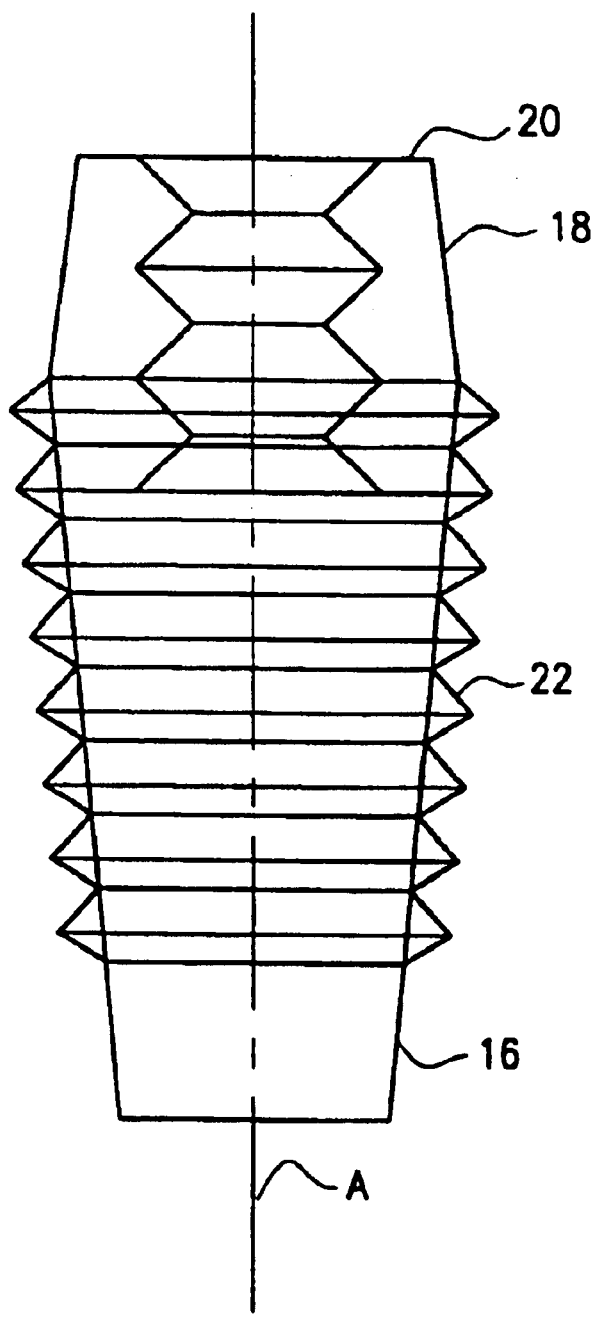
FIG. 9 is a cross-sectional side view of the tapered implant body of FIG. 6 with threads.

Similarly, shown in FIG. 9 is the embodiment illustrated in FIG. 6 with the external threads 22 along the external sidewall 16 of the implant body 12.

Figure 10:
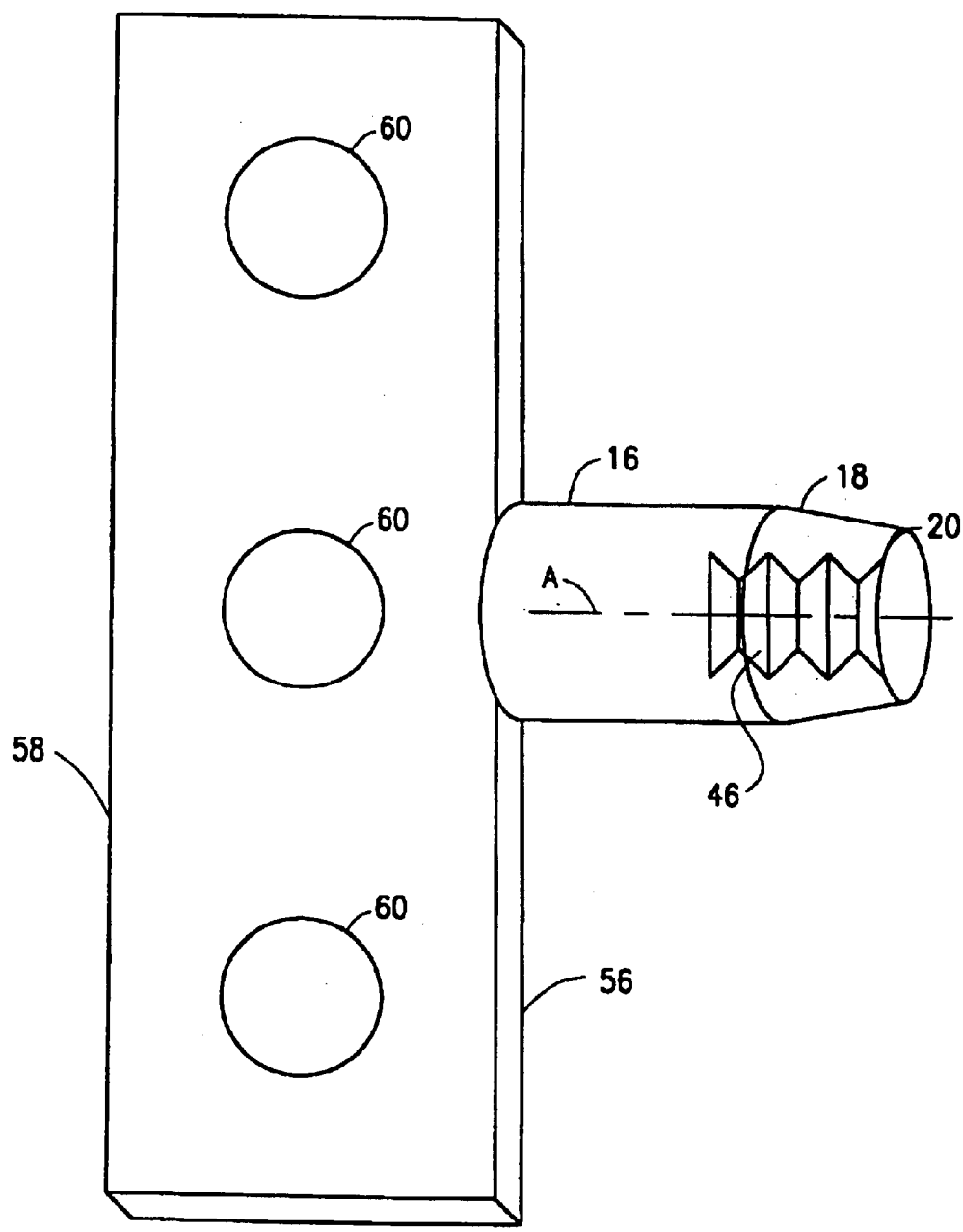
FIG. 10 is a cross-sectional side view of an alternate embodiment of the present invention having a blade portion affixed to the implant body.

With reference now to FIG. 10, there is illustrated an alternative structure for the implant body 12. In particular, the implant body in this embodiment contains a narrow blade-shaped body portion 56 affixed to the heretofore bottom end 24 of the implant body 12. The thin blade body portion 56 has a razor or sharpened edge 58 opposite the fixture of the implant body 12. In use, the blade and implant arrangement is pounded into the jawbone of the patient, securing the implant body 12 portion into bone. A number of holes 60 through the blade 56 allow bone-and tissue growth therethrough, further securing the placement of the implant body 12.

Figure 11:
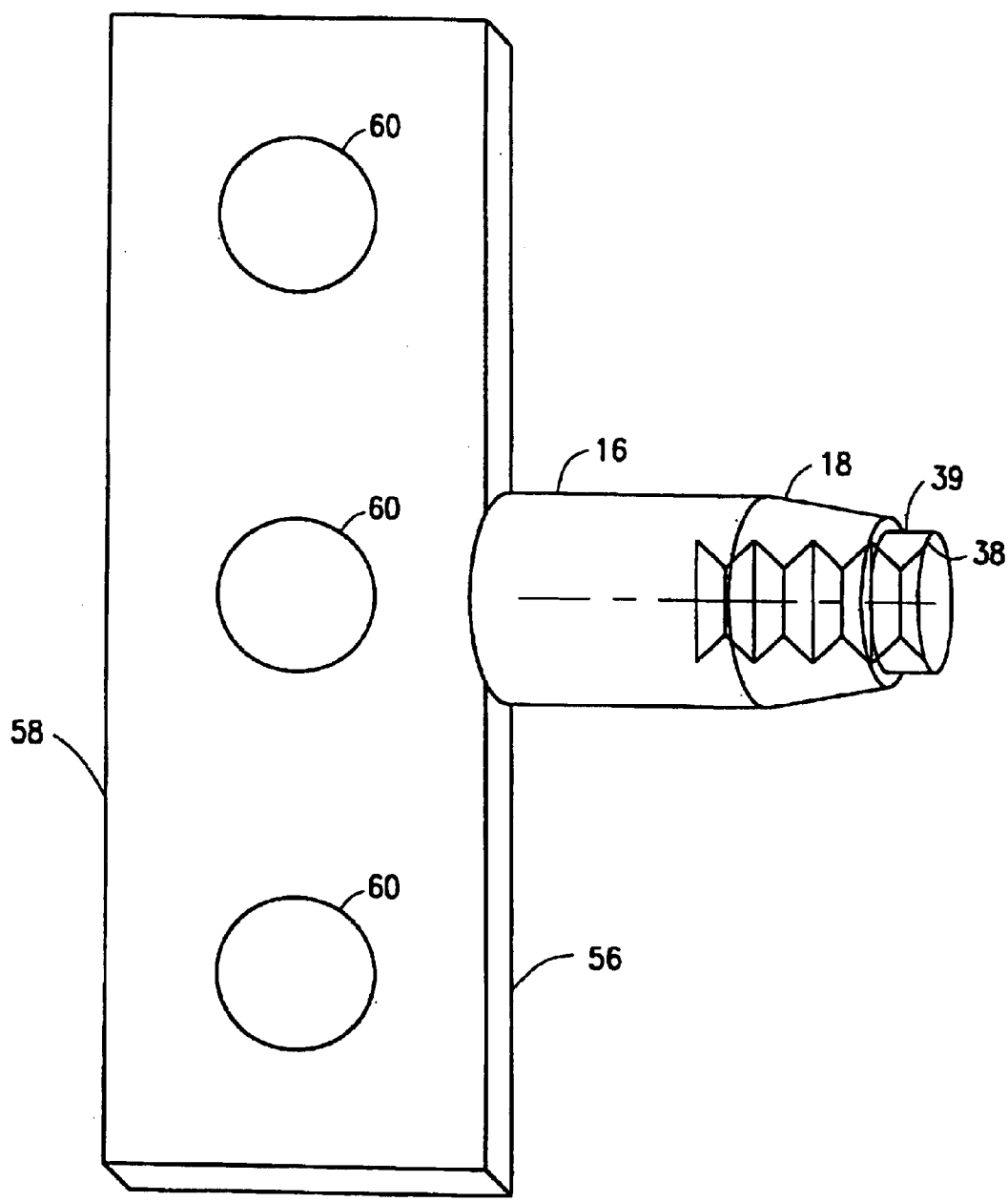
FIG. 11 is a cross-sectional side view of the bladed implant body of FIG. 10 with a projection affixed thereto.

Lastly, shown in FIG. 11 is a modified embodiment of the configuration of FIG. 10 including a projection portion 38 affixed to the top end 20 of the implant body 12, which engages the aforementioned secondary cavity 40 in the manner described hereinabove.

The invention has numerous advantages. One advantage is that the external taper of the external tapered cylindrical surface 18 allows for a narrower implant to be used than may currently be used. In the apparatus of the invention, the abutment 14 surrounds the implant body 12. In some related art devices, the implant system has the opposite configuration, i.e., where the implant body surrounds the abutment. When the implant body surrounds the abutment, it is necessary to make the walls of the implant body very wide to give the implant body enough structural strength to prevent breaking. Further, when the implant body surrounds the abutment, the margin of a prosthesis or crown is on the implant body, which cannot be modified.

In the apparatus of the invention on the other hand, the external taper 18 of the implant body 12 allows for an implant body 12 that is narrow and an abutment 14 that is wider. The wider abutment 14 can be bulky to provide for strength and for aesthetic purposes. Furthermore, the weakest portion of the assembly 30 lies in the abutment 14. In the apparatus of the invention, the abutment 14 is changeable. A changeable embodiment is advantageous because an implant body 12 is difficult to change, i.e., the implant body 12 requires removal if fractured. An externally tapering implant body 12 allows the use of modifiable abutments 14 at a patient's gingival margin. For aesthetic purposes and for creating a shape that does not trap food, it is necessary to have flexibility in the gingival area of the assembly. An externally tapering implant body 12 combined with modifiable abutments 14 is aesthetically desirable and allows for the creation of an implant system that does not trap food.

An additional advantage of the device of the invention is that the device uses a friction-fit taper connection for an anti-rotational connection. A friction-fit taper connection is leak-proof, prevents rotation and provides a connection that takes load off of the fastener 44, thereby preventing micromovement of the abutment 14. A friction fit connection is less likely to experience problems associated with loosening or breakage of the fastener 44 than with non-friction fit connections. The apparatus of the invention possesses the advantages of a friction fit taper connection without the disadvantages associated with an implant body 12 that surround the abutment 14.

A further advantage of the apparatus of the invention is that an externally tapering implant body 12 with an abutment 14 that is secured to the implant by means of a screw 44 with a torque-wrench is more precise and more comfortable to the patient than existing implants that require a non-quantifiable tapping or hammering force to seat the abutment 14.

Another advantage is that an optional projection 38, e.g., a hexagonal projection, provides an additional anti-rotational component, which also allows for precise capturing of orientation of the abutment 14 by means of commonly used impression components, which aids in the fabrication of a prosthesis. The external hexagonal projection 38 is not necessarily engaged because the main stability of the device derives from the tapered friction fit of the anti-rotation connection. All of the positioning advantages of the projection component 38 are available but the disadvantages of loosening or breakage of the screw 44 are eliminated.

While only several forms of the invention have been shown and described, it should be apparent to those skilled in the art that the invention is not so limited, but is susceptible to various changes without departing from the scope of the invention.

What is claimed is:

1. A dental implant system having an implant adapted for insertion in a passage formed in a jawbone of a patient, said implant system comprising:
   an implant body having an external tapered cylindrical surface that tapers outwardly and downwardly from a top end of said implant body, said implant body having a threaded implant passage communicating with said top end, said external tapered cylindrical surface having a taper of about one degree to about eight degrees, said implant body having a projection extending from said top end of said implant body, said projection having a plurality of sidewall surfaces to form a first anti-rotational connection;
   an abutment adapted for use with said implant body, said implant being removably attached to said abutment, said abutment including a primary cavity in communication with a bottom end of said abutment, said primary cavity having an internal tapered cylindrical surface that tapers outwardly and downwardly for mating engagement with said external tapered cylindrical surface of said implant body to form a second anti-rotational connection by frictional engagement between said internal tapered cylindrical surface of said abutment and said external tapered cylindrical surface of said implant body, said internal tapered cylindrical surface having a corresponding taper of about one degree to about eight degrees, said second anti-rotational connection being a locking taper forming a hermetic seal;
   said projection substantially preventing rotation of said abutment when said abutment is seated on said implant body; and
   a fastener that communicates with said abutment and locates within said threaded implant passage for securing said abutment to said implant body, thereby eliminating the need of hammering action to seat said abutment to said implant body to achieve rotational stability.

2. The implant system according to claim 16, further comprising:
   an abutment passage passing through said abutment for receiving said fastener for securing said abutment to said implant body.

3. The implant system according to claim 1, wherein:
   said projection has a plurality of walls, said walls being parallel to a longitudinal axis of said implant body.

4. The implant system according to claim 1, wherein:
   said projection substantially prevents rotation of said abutment when said abutment is seated on said implant body.

5. The implant system according to claim 1, wherein:
   said implant body further comprises an external sidewall surface that is essentially cylindrical-shaped.

6. The implant system according to claim 5, further comprising:
   threads on said external sidewall surface of said implant body.

7. The implant system according to claim 1, wherein, said implant body has a narrow blade-shape.

8. The implant system according to claim 1, further comprising:
   an abutment passage in said abutment for receiving said fastener that secures said abutment to said implant body.

9. The implant system according to claim 1, further comprising:
   an attached fastener extending downward from an upper surface of said primary cavity of said abutment, said attached fastener for engaging said threaded implant passage in said implant body for securing said abutment to said implant body.

10. The implant system according to claim 1, wherein said projection having a plurality of sidewall surfaces has six surfaces.

11. The implant system according to claim 1, wherein said projection having a plurality of sidewall surfaces has four surfaces.

12. The implant system according to claim 1, wherein said projection having a plurality of sidewall surfaces has eight surfaces.

* * * * *

UNITED STATES PATENT AND TRADEMARK OFFICE
CERTIFICATE OF CORRECTION

PATENT NO. : 6,726,481 B1  Page 1 of 1
APPLICATION NO. : 10/084441
DATED : April 27, 2004
INVENTOR(S) : Zickmann et al.

It is certified that error appears in the above-identified patent and that said Letters Patent is hereby corrected as shown below:

On the title page (76), delete "Sheldon Leonard" and insert therefor --Sheldon Lerner--.

Signed and Sealed this

Twenty-ninth Day of January, 2008

JON W. DUDAS
*Director of the United States Patent and Trademark Office*